United States Patent [19]

Hoffman et al.

[11] Patent Number: 5,171,388
[45] Date of Patent: Dec. 15, 1992

[54] APPARATUS FOR AND METHOD OF APPLYING AN ELASTIC MATERIAL TO A FLEXIBLE BACKING

[75] Inventors: John W. Hoffman; Karl R. Dehn, both of Appleton, Wis.

[73] Assignee: Kimberly-Clark Corp., Neenah, Wis.

[21] Appl. No.: 505,954

[22] Filed: Apr. 6, 1990

[51] Int. Cl.⁵ .............................................. B32B 31/04
[52] U.S. Cl. ........................ 156/164; 156/210; 156/265; 156/285; 156/473; 156/547; 156/552
[58] Field of Search .............. 156/164, 210, 229, 265, 156/285, 472, 473, 519, 552, 547; 604/385.2

[56] References Cited

U.S. PATENT DOCUMENTS

| | | | |
|---|---|---|---|
| 3,860,003 | 1/1975 | Buell | 604/385.2 |
| 3,951,150 | 4/1976 | Schaar | 604/285.2 |
| 4,227,952 | 10/1980 | Sabee | 156/164 |
| 4,240,866 | 12/1980 | Rega | 156/496 |
| 4,285,747 | 8/1981 | Rega | 156/164 |
| 4,379,016 | 4/1983 | Stemmler et al. | 156/205 |
| 4,397,704 | 8/1983 | Frick | 156/201 |
| 4,417,935 | 11/1983 | Spencer | 156/80 |
| 4,417,938 | 11/1983 | Sigl | 156/270 |
| 4,425,173 | 1/1984 | Frick | 156/204 |
| 4,481,066 | 11/1984 | Hirakawa et al. | 156/547 |
| 4,488,923 | 12/1984 | Pieniak | 156/199 |
| 4,498,944 | 2/1985 | Krause et al. | 156/205 |
| 4,543,099 | 9/1985 | Bunnelle et al. | 604/385 |
| 4,543,154 | 9/1985 | Reiter | 156/73.1 |
| 4,563,185 | 1/1986 | Reiter | 604/385 |
| 4,574,022 | 3/1986 | Johnson et al. | 156/164 |
| 4,618,384 | 10/1986 | Sabee | 156/205 |

FOREIGN PATENT DOCUMENTS 304044  2/1989  European Pat. Off. .......... 604/385.2

*Primary Examiner*—Michael W. Ball
*Assistant Examiner*—Steven D. Maki
*Attorney, Agent, or Firm*—Thomas J. Connelly

[57] ABSTRACT

An apparatus and method are disclosed for securing elastic to a flexible backing for use in catamenial pads. The apparatus includes means for feeding the backing sheet onto a first drum having a plurality of surface grooves formed therein. The backing sheet is pulled into each of the grooves such as by a vacuum. A strip of elastic is then placed across each of the grooves and anchored at its respective ends. The backing sheet is then drawn off of the drum and extended so that the elastic is stretched to overlay the backing sheet. The apparatus further includes means for adhering portions of the elastic intermediate the anchored ends to the backing sheet while the elastic is in its extended position. The method for applying the elastic material to the backing sheet uses the apparatus discussed above.

34 Claims, 2 Drawing Sheets

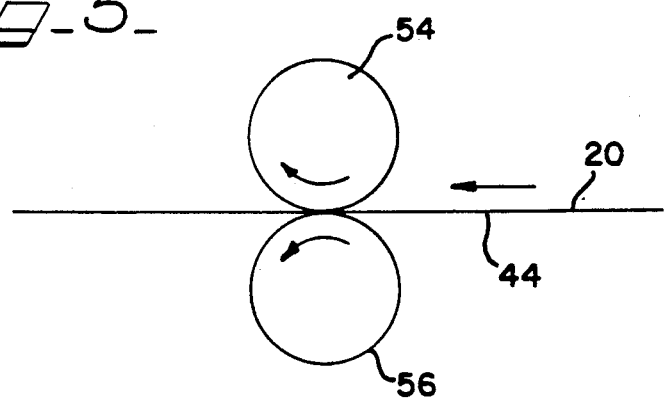
FIG-5-
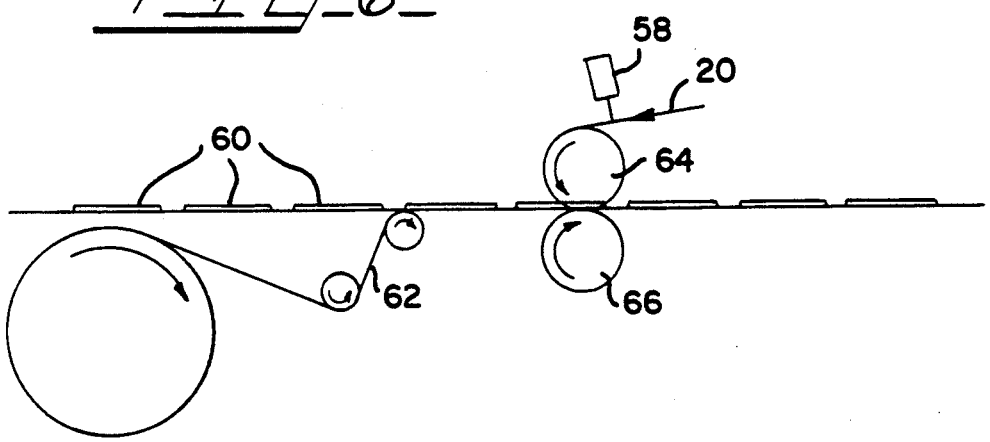
FIG-6-
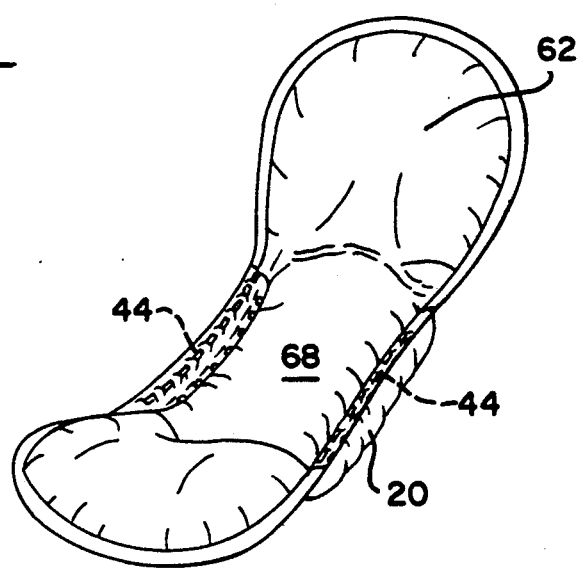
FIG-7-

APPARATUS FOR AND METHOD OF APPLYING AN ELASTIC MATERIAL TO A FLEXIBLE BACKING

FIELD OF THE INVENTION

This invention relates to an apparatus for and method of applying an elastic strip to a flexible backing. It relates in particular to an apparatus for and method of applying elastic strips to flexible plastic backings, such as polyethylene films, to be used in catamenial devices.

BACKGROUND OF THE INVENTION

In diapers, catamenial devices, and other absorbent devices, it is commonplace to have an absorbent material, for example, a batt made from cellulosic fluff, that is backed with a thin plastic film. The backing is supposed to retain moisture in the device. For comfort and additional moisture retention assurance, such devices have been designed to conform to the body. To make such a device conform to the body, an elastic member is often bonded to the plastic backing so as to create pleats or folds in the backing. The elastic is typically bonded to the flat backing while the elastic is stretched. After the elastic is secured, the elastic is released which causes the elastic to contract and gather the flat backing and the absorbent material into a curved shape that conforms to the body.

An example of a device and method of applying elastic to a flexible backing is illustrated in U.S. Pat. No. 4,397,704 issued to Frick on Aug. 9, 1983. This patent teaches that a flexible backing is corrugated by winding the backing onto a drum with corrugations formed in its circumference. While the drum is rotating, unstretched, adhesive-coated elastic strips are applied intermittently onto and perpendicular to the corrugations on the corrugated backing such that the elastic strips adhered only to the peaks, but not the valleys, of the corrugations. After the strips are adhered to the peaks, the flexible backing is unwound from the drum and stretched such that the corrugations are removed and the portions of the strips previously spanning the valleys contact the backing. The elastic is then adhered, along its length, to the stretched backing by passing the backing and elastic through nip rolls. When the assembly is allowed to relax after stretching, the elastic gathers the backing.

A problem with Frick's approach is that each piece of bonded elastic has regions of stretched and unstretched elastic between the ends of the elastic. Therefore, when the elastic strip is stretched to the extent that the flexible backing will permit, the unstretched regions correspond to those areas of the elastic that were originally adhered to the peaks of the corrugations in the unstretched state. The stretched regions correspond to those areas that spanned the valleys of the corrugations. The unstretched regions reduce the effectiveness of the elastic because they do not contribute to the gathering of the backing.

Such a situation can be tolerated in a large absorbent device such as a diaper. The elastic in a diaper is long enough that it can produce the desired curvature with much of the elastic effectively not utilized because it cannot be stretched.

The situation, however, cannot be tolerated in small absorbent devices such as catamenial devices where localized areas of the device have elastic bonded to it. A much larger percentage of stretchable elastic is needed per length of elastic in a small device to produce the body conformity desired.

SUMMARY OF THE INVENTION

With this invention, localized gathering of the flexible backing is possible because all the elastic between the anchored ends of the elastic contributes to stretching. The method of this invention involves feeding the flexible backing material onto a drum that has surface grooves parallel to the axis of the drum such that at least a portion of the flexible backing overlays the drum and the internal surface of at least one of the grooves. The grooves are spaced between about 5 and 25 centimeters (cm) apart on the drum, and each of the grooves has a substantially smooth internal surface with a surface length between about 3 and 24 cm. Each of the grooves is between approximately 2.5 and 7.5 cm wide. Furthermore, the ratio between the surface length and groove width is between about 1.3:1 and 3:1.

At least one elastic strip is placed across the width of the one groove. The elastic strip is anchored at its ends to the flexible backing on the edge of the groove outside the groove so the strip spans the groove. The flexible backing is drawn off the drum and pulled so that the elastic is stretched to overlay the backing. The portion of the elastic located intermediate the anchored ends is adhered to the backing when the intermediate portion is stretched. When the elastic is allowed to relax, it gathers the flexible backing into localized pleats.

The flexible backing is used in small absorbent devices, and the elastic allows the device to conform to the human body.

The general object of this invention is to provide an apparatus and a method for applying an elastic material to a flexible backing. A more specific object of this invention is to provide an apparatus which permits elastic strips to be aligned with and fastened to a backing member.

Another object of this invention is to provide an apparatus which utilizes a drum having a plurality of surface grooves formed therein and into which a backing material can droop.

Still another object of this invention is to provide a simple and economical means of applying elastic strips to a flexible backing material.

Other objects and advantages of the present invention will become more apparent to those skilled in the art in view of the following description and the accompanying drawings.

BRIEF DESCRIPTION OF THE DRAWINGS

FIGS. 2-5 are schematic representations of steps in the process of this invention.

FIG. 6 is a schematic representation of an apparatus for assembling a catamenial device using the flexible backing produced by the apparatus in FIG. 1. and FIG. 7 is a perspective view of a catamenial device produced in accordance with the apparatus and process of this invention.

DETAILED DESCRIPTION OF THE PREFERRED EMBODIMENT

Figure 1:
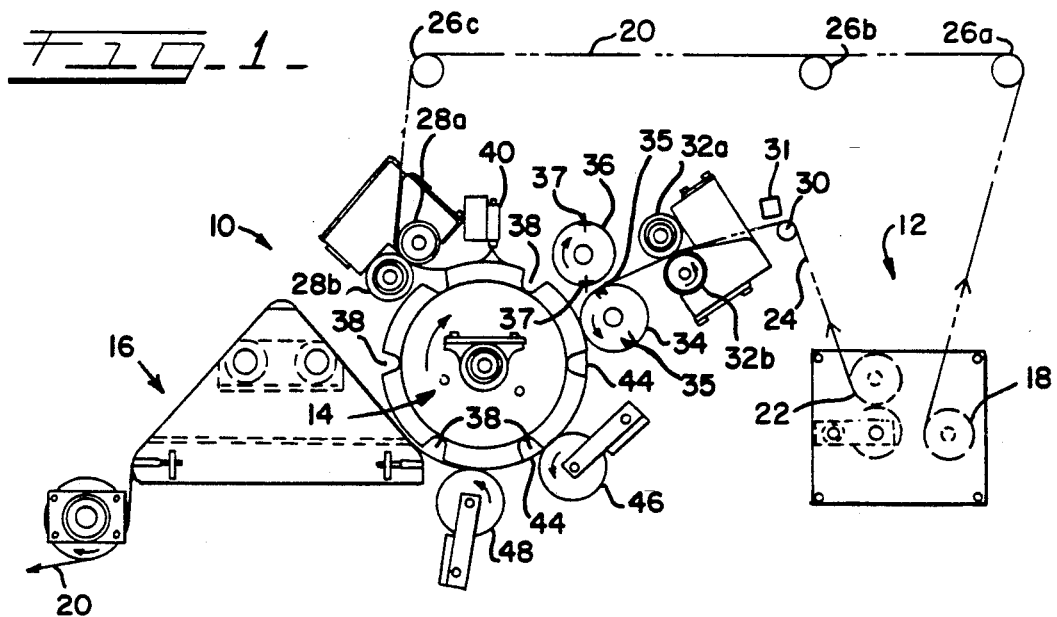
FIG. 1 is a side view of an apparatus for applying an elastic material to a flexible backing.

Referring to FIG. 1, an apparatus 10 for practicing the process of this invention is illustrated. The apparatus 10 includes a feed device 12 for feeding backing and elastic onto a looper drum 14. The looper drum 14 and appurtenant devices apply elastic strips to the backing in a manner described below. The backing is then removed in a continuous sheet from the looper drum 14 by a conveyor 16. The backing is then used for backing catamenial devices as shown in FIG. 7. Feed device 12 includes a first dispensing roll 18 for dispensing a flexible backing sheet material 20. The backing sheet 20 is preferably a thin sheet of polyethylene, for example, about 0.5 to 3 millimeters (mm) thick and about 5 to 20 cm. wide. The backing sheet 20 is passed above apparatus 10 on a series of guide rolls 26a, 26b and 26c, and fed between a pair of motor-driven nip rolls 28a and 28b. The nip rolls 28a and 28b draw the backing sheet 20 from the feed roll 18 and over the guide rolls 26a, 26b and 26c, and feed the backing sheet 20 onto the looper drum 14.

The feed device 12 also includes a second dispensing roll 22 for dispensing an elastic strip material 24. The elastic strip 24 is preferably made from stretch bonded laminate (SBL), and comes in a continuous strip that is about 4 centimeters (cm) wide. The elastic material 24 is drawn across a guide roll 30 by a pair of motor-driven nip rolls 32a and 32b. As the elastic strip 24 is drawn across the guide roll 30 it is cut lengthwise by a score slitter 31, which is mounted adjacent to the roll 30, into two approximately 2 cm wide continuous parallel strips. The two strips are pass between the nip rolls 32a and 32b and then between a vacuum transfer drum 34 and an elastic cutter 36 described in more detail below. The elastic cutter 36 cuts the two parallel elastic strips simultaneously, and the vacuum transfer drum 34 transfers the two strips onto the looper drum 14.

The looper drum 14 is a cylindrical drum that is rotated around its longitudinal axis by a motor (not shown). The looper drum 14 has a plurality of grooves 38 that are formed parallel to the longitudinal axis of the drum 14 and spaced equidistant from each other around the circumference of the looper drum 14, about 5 to 25 cm apart. The looper drum 14 has vacuum suction means that operate to draw suction through the surface thereof at locations and times described below.

The looper drum 14 is rotated clockwise when viewed from the side shown in FIG. 1. The backing sheet 20 is fed onto the surface of the looper drum 14 by the nip rolls 28a and 28b that are positioned at approximately the 11 o'clock position relative to the drum 14. A vacuum is applied to that portion of the drum 14 starting between the 11 and 12 o'clock positions, and the vacuum is ended at about the six o'clock position. No vacuum is applied to the surface of the drum 14 between the six o'clock position and the vacuum start position.

Figure 2:
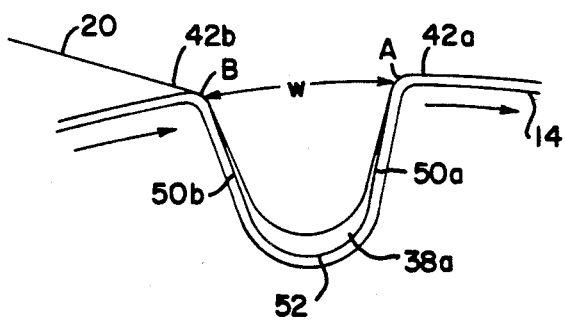

The operation of the looper drum 14 can be understood by following one groove 38a as it rotates from the 12 o'clock position clockwise. As the backing sheet 20 is fed onto the surface of the looper drum 14, the vacuum draws a portion of the backing sheet 20 into a groove 38a at the 12 o'clock position as shown in FIG. 2.

Preferably the vacuum is drawn at a pressure of between about 1000 and 5000 torr. The nip rolls 28a and 28b feed the backing sheet 20 at a rate that allows the necessary backing sheet 20 to be drawn into the groove 38a without noticeable stretching of the backing sheet 20. The feed rate of the nip rolls 28a and 28b is not so fast that the backing sheet material 20 between adjacent grooves 38 cannot lay smooth on the surface of the looper drum 14.

As the groove 38a passes the 12 o'clock position, a pressure-sensitive adhesive is sprayed from a stationary adhesive gun 40 in two spaced parallel strips, for example, in strips where the elastic will be secured as described below, that are between about 0.5 and 18 cm apart, preferably 6 cm apart. The adhesive is preferably a sprayable, pressure-sensitive type, for example, adhesive 70-3166 from National Starch Corporation. The adhesive has a shear force of between 1000 and 4000 grams as measured by an Instron machine. Each strip of adhesive is applied into the groove 38a and on anchor areas 42a and 42b on either side and outside of the groove 38a on the surface of the looper drum 14. The adhesive is not otherwise applied to the backing sheet 20 on the surface of the looper drum 14. The stationary adhesive gun 40 allows more adhesive to be applied per unit area on the anchor areas 42a and 42b than on the backing sheet 20 lining the groove 38a. The reason for this is that the looper drum 14 is rotated at a constant speed under the adhesive gun 40 while the adhesive is sprayed on at a constant rate. Since there is more area in the groove 38a to cover with adhesive per unit time than on the anchor areas 42a and 42b, the backing sheet 20 receives less adhesive. The advantages of this difference in adhesive application will be explained below.

Figure 3:
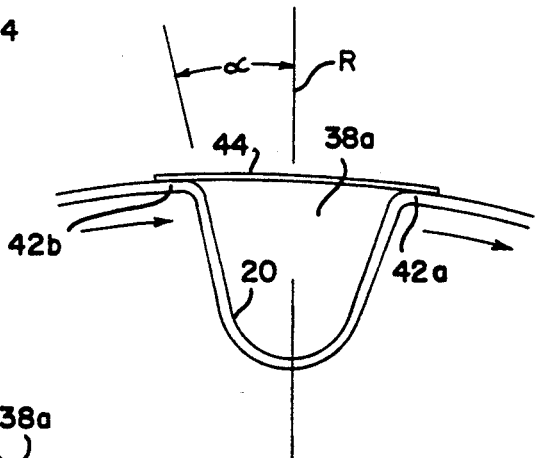

As the groove 38a passes the 2 o'clock position, the vacuum transfer drum 34 simultaneously transfers onto the looper drum 14 two strips of elastic 44. The elastic strips 44 are cut from the continuous elastic strip 24 such that the two strips 44 are parallel to one another and span the groove 38a, as is shown in FIG. 3. Only one of the elastic strips 44 is shown in FIG. 3. Each of the elastic strips 44 is positioned such that its ends overlay the adhesive-coated anchor areas 42a and 42b. Each elastic strip 44 is positioned such that between about 0.3 and 2.5 cm of each end overlays the anchor areas 42a and 42b. As shown in FIG. 1, the vacuum transfer drum 34 is close to the looper drum 14. The gap between the surfaces of the two drums 34 and 14 is about 0.5 to 3.0 times the thickness of the elastic. The elastic strips 44 are applied such that they pass through this gap, which compresses the ends of elastic strips 44 against the anchor areas 42a and 42b. This ratio of gap thickness to elastic thickness has been found to provide an initial attachment of elastic to the backing sheet 20 without compressing the backing sheet 20 and the elastic unduly to cause adhesive to ooze from between them.

The elastic is preferably a stretch bonded laminate type, for example, from Kimberly-Clark Corp., and has a modulus of elasticity between about 80 N/m$^2$ to about 120 N/m$^2$. When the elastic is stretched 100%, it has a tension ranging between about 350 and 450 grams per inch width of the elastic.

Nip rolls 46 and 48 are positioned at about the four o'clock and about the six o'clock positions. The nip roll 46 further compresses the elastic strips 44 onto the anchor areas 42a and 42b. The nip roll 48 isolates the nip roll 46 from the tension exerted on the backing sheet 20 by the conveyor 16. After the six o'clock position, the vacuum exerted on the groove 38a is released, and the backing sheet 20 is removed from the looper drum 14 in a manner described below.

The grooves 38 on the looper drum 14 should have a substantially smooth internal surface. The "internal surface" is the area between points A and B along the surface of the groove shown in FIG. 2. By "substantially smooth" is meant that there are no sharp contours that prevent the backing sheet 20 from conforming to the contours of the internal surface of the groove 38. As shown in FIG. 2, for example, the groove 38a has two flat sidewalls 50a and 50b that slope toward one another as they go deeper into the groove 38. The sidewalls 50a and 50b slope at an angle alpha, (see FIG. 3) between about 5 and 20 degrees as measured from a radius R drawn through the middle of the groove 38. The bottom ends of the sidewalls 50a and 50b are joined by a curved portion 52. Therefore, as the backing sheet 20 is drawn into the groove 38a under vacuum, the backing sheet 20 will slide into and conform to the groove 38. If the groove 38 were not substantially smooth, then too little backing sheet material 20 may be drawn into the grooves 38, or different amounts of material will be drawn into the several grooves 38. If too little backing sheet material 20 is drawn into the grooves 38, that affects the degree of gathering of the backing sheet material 20. If different amounts of backing sheet material 20 are drawn into the several grooves 38, that may adversely affects the positioning of the elastic as well.

The grooves 38 also have a surface length from about 3 to 24 cm long, preferably from about 5 to 15 cm long. By "surface length" is meant the length of the surface of the groove 38a between points A and B in FIG. 2. The grooves 38 also have a width W between points A and B of between about 2.5 and 7.5 cm., preferably between about 4 and 7 cm. Most importantly, the ratio between the surface length and groove width is between about 1.3:1 and 3:1, preferably between about 1.75:1 and 2:1.

The elastic strips 44 are produced from the elastic material 24. As indicated above, the elastic material 24 is slit with a stationary knife 31 longitudinally into two parallel strips, each of which is about 2 cm. wide. The two parallel strips are spread about 5 cm apart, and fed between the nip rolls 32a and 32b. The nip rolls 32a and 32b are rotated stepwise at the same speed. Their speed is controlled by an optical sensor that senses the rotational speed and position of the looper drum 14. The speed of the nip rolls 32a and 32b are controlled such that only about 6 cm lengths of elastic are fed to the vacuum transfer drum 34 and to the cutter 36 for every groove 38 that passes the vacuum transfer drum 34.

The vacuum transfer drum 34 has a pair of cutting mandrels 35 that are spaced 180 degrees apart on the cylindrical surface. The mandrels 35 contact the cutter blades 37 that protrude from the surface of the cutter drum 36. The cutter drum 36 is driven synchronously with the vacuum transfer drum 34 so that as the approximately 6 cm lengths of elastic are fed between the vacuum transfer drum 34 and the cutter drum 36 by the nips 32a and 32b, a cutter blade 37 will contact the mandrel 35 to sever the two long strips of elastic 44 (see FIGS. 1 and 3). The vacuum transfer drum 34 includes a vacuum device that holds the elastic strips 44 onto the surface of the vacuum transfer drum 34 until the drum 34 rotates so that the elastic strips 44 are between the vacuum transfer drum 34 and the looper drum 14. The vacuum is then released from the elastic strips 44, and the elastic strips 44 are compressed against and adhered to the anchor areas 42a and 42b on the backing sheet 20 as described previously. The vacuum transfer drum 34 is driven synchronously with the looper drum 14 so that they rotate at the same angular speed. The "same angular speed" means that their surfaces travel at the same velocity.

Figure 4:
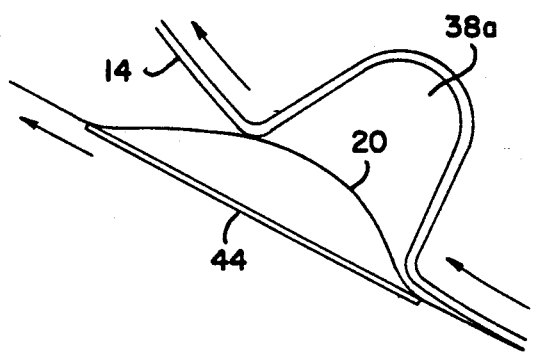

The tension on the backing sheet 20, as it is removed from the looper drum 14, is caused by the conveyor 16 removing the backing sheet 20 from the looper drum 14 at a speed 5% greater than the speed of feeding the backing sheet 20 onto the looper drum 14. It was found necessary to do this to stretch the elastic strips 44 between the anchor areas 42a and 42b so that the elastic overlays the backing sheet material 20 that was gathered into the groove 38a, (see FIG. 5). The stretching of the elastic begins as the backing sheet 20 is removed from the looper drum 14 (see FIG. 4) and has to be completed before the backing sheet 20 is drawn through a pair of nip rolls 54 and 56 (see FIG. 5) in the conveyor 16. The nip rolls 54 and 56 compress the stretched elastic against the backing sheet 20 such that the adhesive applied between the anchor areas 42a and 42b, for example, the adhesive applied to the backing sheet 20 that was once in the groove 38a, can adhere the elastic to the backing sheet 20 between the anchor areas.

After the backing sheet 20 is passed through the nip rolls 54 and 56 and through the conveyor 16, a construction adhesive is applied with an adhesive gun 58 (see FIG. 6) across the entire surface of the backing sheet 20 on which the elastic strips 44 are adhered.

Referring to FIG. 6, absorbent pads 60 are spaced along a conveyor (not shown) and fed by the conveyor onto a continuous sheet of cover material 62 which is moving at the same speed as the conveyor. The backing material 20, which is still under tension to keep the elastic strips 44 stretched, is fed at the same speed as the cover material 62 through a pair of nip rolls 64 and 66. The adhesive previously sprayed onto the backing sheet 20 adheres the absorbent pads 60 onto the backing sheet 20 and adheres the cover material 62 to the backing sheet 20 around the perimeters of the absorbent pads 60. It should be noted that the absorbent pads 60 are narrower than the width of the backing sheet 20 and the cover sheet 62.

Referring to FIG. 7, a finished catamenial pad 68 is shown which has been die cut from the web of material passed through the nip rolls 64 and 66. Each finished pad 68 has two parallel elastic strips 44 that gather the otherwise planar product into a curved absorbent pad 68. The elastic strips 44 form part of the perimeter of the catamenial pads 68, and are centered along the middle edges of the pad with the absorbent pad 60 positioned therebetween. As can also be seen, the backing sheet 20 is adhered about its perimeter to the cover sheet 62. Preferably, the cover sheet 62 is made from a spunbonded material that allows moisture to flow easily through, so that it can be absorbed by the absorbent pad 60. The catamenial pad 68 is constructed otherwise as taught in U.S. Pat. No. 4,770,657 issued to Ellis et al. on Sep. 13, 1988, and which is incorporated by reference and made a part hereof.

While the invention has been described in conjunction with a specific embodiment, it is to be understood that many alternatives, modifications and variations will be apparent to those skilled in the art in light of the foregoing description. Accordingly, this invention is intended to embrace all such alternatives, modifications and variations which fall within the spirit and the scope of the appended claims.

We claim:

1. A method of applying an elastic material to a flexible backing material, comprising:
   a) feeding said flexible backing material onto a rotatable drum having a plurality of grooves formed therein which are aligned parallel to the central axis of said drum, said grooves being spaced apart between about 5-25 centimeters, each groove having a substantially smooth internal surface with a surface length of between about 3-24 centimeters, a width of between about 2.5-7.5 centimeters, and a ratio of surface length to width of between about 1.3-3.1 to 1, said flexible backing material overlaying said internal surface of said grooves;

b) applying adhesive onto said flexible backing material at a constant rate whereby a lesser amount of adhesive contacts said backing material positioned within said groove than at anchor areas located outside of said groove;

c) positioning an unstretched strip of elastic material across the width of only one of said grooves, said strip having spaced apart opposite ends;

d) securing said opposite ends of said strip of elastic material by said adhesive to said flexible backing material at said anchor areas such that said strip spans across said one groove;

e) pulling said flexible backing material from said drum whereby said flexible backing material is extended and said strip of elastic material is stretched over said flexible backing material; and f) securing said stretched strip of elastic material by said adhesive to said flexible backing material intermediate said ends.

2. The method of claim 1 wherein said ends of said strip of elastic material are secured to said flexible backing material by a pressure sensitive adhesive.

3. The method of claim 1 wherein said ends of said strip of elastic material are secured to said flexible backing material by spraying a pressure sensitive adhesive onto said flexible backing material, placing said strip of elastic material onto said flexible backing material and applying pressure to said strip of elastic material.

4. The method of claim 3 wherein said strip of elastic material has a modulus of elasticity from about 80 N/m$^2$ to about 120 N/m$^2$.

5. The method of claim 3 wherein said adhesive has a shear force between about 1000 and 4000 grams.

6. The method of claim 1 wherein said strip of elastic material is adhered to said flexible backing material intermediate said ends with a pressure sensitive adhesive.

7. The method of claim 6 wherein said adhesive is sprayed onto said flexible backing material while said material is rotating on said drum.

8. The method of claim 7 wherein said adhesive is applied onto said flexible backing material to ensure that the ends of said strip of elastic material will adhere stronger to said flexible backing material than points intermediate said ends.

9. The method of claim 1 wherein each of said grooves has a pair of flat sides that slope upwardly and outwardly from a bottom surface of said groove and arcuate portions which join said flat sides to said bottom surface.

10. The method of claim 9 wherein each of said flat sides slope at an angle of between about 5-20 degrees into said groove.

11. The method of claim 1 wherein said drum includes vacuum means, and said method further comprises drawing a vacuum on said drum whereby said flexible backing material is retained on said drum and drawn into said grooves.

12. The method of claim 11 wherein said vacuum is drawn between about 1000 and 5000 torr.

13. The method of claim 1 wherein said strip of elastic material is fed from a supply roll to a cutter where it is cut into discrete strips.

14. The method of claim 13 wherein said drum and a transfer drum are rotated at the same angular speed and a nip is present therebetween of between about 0.25 to 3 times the thickness of said strip of elastic material, and said method further comprises passing said strip of elastic material through said nip.

15. The method of claim 14 wherein said strip of elastic material is anchored at its ends to said flexible elastic material by applying a pressure-sensitive adhesive onto said flexible backing material before said strip of elastic material is placed thereon.

16. The method of claim 15 wherein said adhesive is sprayed onto said flexible backing material as said drum is rotated such that said adhesive is applied where the ends of said strip of elastic material are to be anchored as well as onto the portion of said flexible backing material located in said groove.

17. The method of claim 16 further comprising compressing the ends of said strip of elastic material against said flexible backing material after said strip of elastic material and said flexible backing material have passed through said nip.

18. The method of claim 17 wherein said ends of said strip of elastic material are compressed by passing said strip of elastic material and said flexible backing material between a first nip roll and said drum.

19. The method of claim 18 wherein said strip of elastic material and flexible backing material are passed between a second nip roll and said drum before said flexible backing material is drawn off of said drum.

20. An apparatus for applying a strip of elastic material to a flexible backing material, comprising:

a) a rotatable drum having a circumferential surface with a plurality of grooves formed therein which are aligned parallel to the central axis of said drum, said grooves being spaced apart between about 5-25 centimeters, each of said grooves having a substantially smooth internal surface with a surface length of between about 3-24 centimeters, a width of between about 2.5-7.5 centimeters, and a ratio of surface length to width of between about 1.3-3.1 to 1;

b) means for applying adhesive onto said flexible backing material at a constant rate whereby a lesser amount of adhesive contacts said backing material positioned within said groove than at anchor areas located outside of said groove;

c) means for feeding said flexible backing material onto said circumferential surface of said drum such that said flexible backing material overlays said internal surface of said grooves;

d) means for placing an unstretched strip of elastic material across the width of only one of said grooves, said strip having spaced apart opposite ends;

e) means for securing said opposite ends of said strip of elastic material by adhesive to said flexible backing material at said anchor areas such that said strip spans across said one groove;

f) means for pulling said flexible backing material from said drum whereby said flexible backing material is extended and said strip of elastic material is stretched over said flexible backing material; and g) means for securing said strip of elastic material by adhesive to said flexible backing material intermediate said ends.

21. The apparatus of claim 20 wherein said means for applying adhesive comprises an adhesive spray gun and said means for securing said opposite ends of said strip of elastic material to said flexible backing material comprises means for applying pressure to said strip of elastic material downstream of said adhesive spray gun.

22. The apparatus of claim 21 wherein said adhesive spray gun is stationary and adhesive is sprayed onto said flexible backing material while said drum is rotated.

23. The apparatus of claim 20 wherein each of said grooves is constructed with a pair of flat sides that slope upwardly and outwardly from a bottom surface of said groove, and said flat sides are joined to said bottom surface by an arcuate portion.

24. The apparatus of claim 23 wherein each of said flat sides slopes at an angle of between about 5-20 degrees into said groove.

25. The apparatus of claim 20 wherein said drum includes vacuum means and said flexible backing material is retained on said drum and drawn into at least one of said grooves by said vacuum means.

26. The apparatus of claim 20 further including cutter means for cutting said strip of elastic material into discrete strips.

27. The apparatus of claim 26 further including drive means for rotating said drum and a transfer drum at a predetermined angular speed and a nip is formed between said drum and said transfer drum which is between about 0.25 to 3 times the thickness of said strip of elastic material, and said strip of elastic material is positioned onto said drum by passing through said nip.

28. The apparatus of claim 27 wherein said means for securing said opposite ends of said strip of elastic material to said flexible backing material comprises means for compressing said opposite ends of said strip of elastic material against said drum after said strip of elastic material has passed through said nip.

29. The apparatus of claim 28 wherein said compressing means includes a first nip roll.

30. The apparatus of claim 29 wherein said compressing means strip and includes a second nip roll.

31. A method of applying an elastic material to a flexible backing material, comprising:
   a) feeding said flexible backing material onto a rotatable drum having a plurality of grooves formed therein which are aligned parallel to the central axis of said drum, said grooves being spaced apart between about 5-25 centimeters, each groove having a substantially smooth internal surface with a surface length of between about 3-24 centimeters, a width of between about 2.5-7.5 centimeters, and a ratio of surface length to width of between about 1.3-3 to 1, said flexible backing material overlaying said internal surface of said grooves;
   b) applying adhesive onto said flexible backing material at a constant rate whereby a lesser amount of adhesive contacts said backing material positioned within said groove than at anchor areas located outside of said groove;
   c) positioning an unstretched strip of elastic material across the width of only one of said grooves, said strip having spaced apart opposite ends and having a modulus of elasticity of between about 80 $N/m^2$-120 $N/m^2$ across the width of said one groove;
   d) securing said opposite ends of said strip of elastic material to said flexible backing material with adhesive at said anchor areas such that said strip spans across only said one groove, said adhesive having a shear force of between about 1000-4000 grams;
   e) pulling said flexible backing from said drum whereby said flexible backing material is extended and said strip of elastic material is stretched over said flexible backing material; and
   f) securing said stretched strip of elastic material by said adhesive to said flexible backing material intermediate said ends.

32. The method of claim 31 wherein said adhesive is sprayed onto said flexible backing material while said flexible backing material is rotating on said drum.

33. The method of claim 32 wherein said adhesive is applied onto said flexible backing material to ensure that the ends of said strip of elastic material will adhere stronger to said flexible backing material than points intermediate said ends.

34. An apparatus for applying a strip of elastic material to a flexible backing material, comprising:
   a) a rotatable drum having a circumferential surface with a plurality of grooves formed therein which are aligned parallel to the central axis of said drum, said grooves being spaced apart between about 5-25 centimeters, each of said grooves having a substantially smooth internal surface with a surface length of between about 3-24 centimeters, a width of between about 2.5-7.5 centimeters, and a ratio of surface length to width of between about 1.3-3.1 to 1;
   b) means for feeding said flexible backing material onto said circumferential surface of said drum such that said flexible backing material overlays said internal surface of said grooves;
   c) a stationary adhesive gun aligned to spray adhesive onto said flexible backing material at a constant rate as said drum is rotated whereby more adhesive per unit area is applied to those portions of said backing material which are located outside of said grooves;
   d) means for placing an unstretched strip of elastic material across the width of only one of said grooves, said strip of elastic material having spaced apart opposite ends which are adhered to said flexible backing material by said adhesive at said anchor areas;
   e) means for pulling said flexible backing material from said drum whereby said flexible backing material is extended and said strip of elastic material is stretched over said flexible backing material; and
   f) means for securing said stretched strip of elastic material by adhesive to said flexible backing material intermediate said ends.

* * * * *